United States Patent [19]

Sumimoto Shinzaburo et al.

[11] Patent Number: 4,910,326

[45] Date of Patent: Mar. 20, 1990

[54] β-KETONITRILS

[75] Inventors: Sumimoto Shinzaburo, Ashiya; Ichiro Ishizuka, Toyono; Hiroyuki Kai, Koka; Shiro Ueda, Osaka; Akira Takase, Kobe, all of Japan

[73] Assignee: Shionogi & Co., Ltd., Osaka, Japan

[21] Appl. No.: 166,306

[22] Filed: Mar. 10, 1988

Related U.S. Application Data

[62] Division of Ser. No. 921,415, Oct. 22, 1986, Pat. No. 4,797,492.

[30] Foreign Application Priority Data

Oct. 23, 1985 [JP]  Japan ................................ 60-238344

[51] Int. Cl.$^4$ ........................................... C07C 120/00
[52] U.S. Cl. ..................................... 558/378; 558/440
[58] Field of Search ................................ 558/440, 378

[56] References Cited

U.S. PATENT DOCUMENTS 4,705,650  11/1987  Mignani et al. ................ 558/440 X
4,728,743   3/1988  Drauz et al. ................... 558/440 X

FOREIGN PATENT DOCUMENTS 0042732A  12/1981  European Pat. Off. .
2230644A  12/1974  France .
2078739A   1/1982  United Kingdom .

*Primary Examiner*—Joseph Paul Brust
*Attorney, Agent, or Firm*—Wenderoth, Lind & Ponack

[57]  ABSTRACT

A fluorinated β-ketonitrile of the formula:

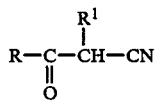

in which: R is alkyl having plural fluorines and $R^1$ is hydrogen or alkyl.

4 Claims, No Drawings

β-KETONITRILS

CROSS-REFERENCE TO RELATED APPLICATION

This application is a divisional application of applicants' copending application Ser. No. 921,415, filed Oct. 22, 1986, now U.S. Pat. No. 4,797,492.

FIELD OF THE INVENTION

The present invention relates to a novel β-ketonitrile which is useful as a raw material for synthesizing pesticides such as herbicides, fungicides and bactericides, and medicines having isoxazolyl group.

BACKGROUND OF THE INVENTION

Various herbicides, fungicides, bactericides etc. having isoxazolyl group have been provided. For example, U.S. Pat. Nos. 4,268,679, 4,507,145 and 4,336,264, and EP-A Nos. 44185 and 49071 disclose various isoxazolylamines as intermediates for their synthesis. However, isoxazolylamines having alkyl group substituted by plural fluorine atoms are not found in the prior art.

SUMMARY OF THE INVENTION

The present invention provides a β-ketonitrile of the formula:

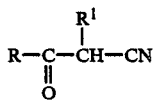
[I]

in which R is alkyl having plural fluorine atoms and $R^1$ is hydrogen or alkyl, which is useful as a raw material for synthesizing such novel isoxazolylamines.

DETAILED DESCRIPTION OF THE INVENTION

A corresponding compound of the formula [I] in which $R^1$ is phenyl or substituted phenyl is known (Chemical Abstracts 70(21): 96286s, ibid. 95(21): 186755q, ibid. 102(9): 78829w etc.) and can be prepared according to the method described by W. R. Nes and A. Barger, J. Am. Chem. Soc., 72, 5409(1950). However, the compound of the formula [I] has not been reported until now and are the novel compound preparing by a process different from a process for preparing a compound of the formula [I] in which $R^1$ is phenyl or substituted phenyl.

Example of alkyl groups having plural fluorine atoms in R includes perfluorinated alkyl groups having 1-9 fluorine atoms and 1-4 carbon atoms, for example, trifluoromethyl, pentafluoroethyl, heptafluoropropyl and 2-(trifluoromethyl)propyl. Examples of alkyl for $R^1$ includes $C_{1-5}$ alkyl, for example, methyl, ethyl, isopropyl and tert-butyl.

The compound of the formula [I] can be prepared by the condensation reaction of the compound of the formula:

$RCO_2R^3$ [II]

in which R is as defined hereinbefore and $R^3$ is alkyl, with the compound of the formula:

$R^1CH_2CN$ [III]

in which $R^1$ is as defined hereinbefore, in the presence of lithium diisopropylamide in tetrahydrofuran. Preferably, the condensation reaction is carried out in a solvent such as tetrahydrofuran or diethyl ether at −78°–0° C. The β-ketonitrile obtained is somewhat unstable but can be stably handled in the presence of a slight amount of toluenesulfonic acid or mineral acid. By the way, preferably, the β-ketonitrile obtained is employed as it is without any purification for a further reaction, because, when it is purified by distillation, a part of it decomposes.

The compound of formula [I] of the present invention is useful for preparing a polyfluoroalkylisoxazolylamine of the formula:

[IV]

in which R and $R^1$ are as defined hereinbefore and $R^2$ is hydrogen or alkyl, or a salt thereof such as hydrochloride, nitrate, acetate, p-toluenesulfonate and methanesulfonate, which is useful as a novel intermediate for synthesizing pesticides and medicines having isoxazolyl group.

The compound of the formula [IV] can be prepared by reacting the β-ketonitrile of the formula [I] with hydroxylamine, hydroxylamine hydrochloride, hydroxylamine sulfate or hydroxyurea etc.

Preferably, this reaction is carried out in a solvent such as water, methanol, ethanol or ethylene glycol by converting the starting material to the corresponding free base by treatment with an alkali such as sodium bicarbonate, sodium carbonate or sodium hydroxide as necessary and thereafter by heating to 60°–120° C. and thereafter by adding 5–36% hydrochloric acid (1–2 eq.) and thereafter by heating to 60°–120° C.

The compound of the formula [IV] is useful as an intermediate for synthesizing pesticides such as herbicides, fungicides and bactericides, and medicines, in particular, herbicides and fungicides.

The following examples and preparations further illustrate the present invention in detail but are not to be construed to limit the scope thereof.

EXAMPLE 1

Trifluoroacetoacetonitrile

A solution of n-butyllithium in n-hexane (280 ml, 0.44 mole) was added to dry diisopropylamine (64 ml, 0.46 mole) dissolved in dry tetrahydrofuran (400 ml), while maintaining the mixture below 0° C. After stirring at 0° C. for 30 minutes, the mixture was cooled below −72° C. A solution of methyl trifluoroacetate (25.61 g, 0.200 mole), acetonitrile (16.42 g, 0.40 mole) in dry tetrahydrofuran (200 ml) were added dropwise, while maintaining the mixture below −72° C. and after maintaining the mixture at the same temperature for additional 45 minutes, it was warmed to room temperature over 1 hour. Ice-water (700 ml) was added to the mixture and tetrahydrofuran and n-hexane were then evaporated under reduced pressure at a bath temperature of 40° C. The residue was extracted with diethyl ether to remove neutral and basic components, adjusted to pH 1 with 36% HCl and then extracted with methylene chloride to remove by-products such as acetoacetonitrile, etc.

The solution was extracted with diethyl ether. After the extract was dried with anhydrous sodium sulfate, p-toluenesulfonic acid (40 mg, 0.0002 mole) was added to the extract. The extract was distilled under the atmospheric pressure and then distilled under reduced pressure to give 26.82 g (crude yield 97.8%) of a cured product. This product was further distilled under reduced pressure to give 16.78 g (61.2%) of the title compound, b.p. 37° C./2.4 mmHg–43° C./2.5 mmHg. When the resulting compound was dissolved in d$^6$-acetone and its NMR was measured, the ratio of the keto form/the enol form was found to be 17/83.

EXAMPLE 2

Pentafluoropropionylacetonitrile

Acetonitrile (4.1 g, 0.10 mole), ethyl pentafluoropropionate (9.61 g, 0.05 mole) and a solution of n-butyllithium in n-hexane (70 ml, 0.11 mole) were reacted according to the same procedure as described in Example 1 to give 7.28 g (77.8%) of the title compound. When the resulting compound was dissolved in CDCl$_3$ and its NMR was measured, the ratio of the keto form/the enol form was found to be 26/74, m.p. 47°–54° C. (deliquescence), b.p. 69°–71° C./18 mmHg.

Anal. Calcd. for C$_5$H$_2$NOF$_5$1/7H$_2$O: C, 31.66; H, 1.22; N, 7.39. Found: C, 31.65; H, 1.59; N, 7.23.

EXAMPLE 3

2-(Trifluoroaceto)propionitrile (a) Propionitrile (19.8 g, 0.36 mole), methyl trifluoroacetate (23.05 g, 0.18 mole) and a solution of n-butyllithium in n-hexane (252 ml, 0.396 mole) were reacted according to the same procedure as described in Example 1 to give 27.72 g (100%) of the title compound. When the resulting compound was dissolved in CDCl$_3$ and its NMR was measured, the ratio of the keto form/the enol form was found to be 49/51, b.p. 52°–57° C./2.7 mmHg.

(b) The title compound was obtained according to the same procedure as in (a) except that methyl trifluoroacetate was replaced with t-butyl trifluoroacetate. Yield: 14.70 g (54.1%).

EXAMPLE 4

2-(Pentafluoropropionyl)propionitrile

Propionitrile (13.2 g, 0.24 mole), ethyl pentafluoropropionate (23.05 g, 0.12 mole) and a solution of n-butyllithium in n-hexane (168 ml, 0.264 mole) were reacted according to the same procedure as described in Example 1 to give 22.72 g (crude yield 94.1%) of the crude title compound. The yield calculated as the pure product was 84.1%. When the resulting compound was dissolved in CDCl$_3$ and its NMR was measured, the ratio of the keto form/the enol form was found to be 71/29, b.p. 63°–65° C./28 mmHg.

Anal. Calcd. for C$_6$H$_4$NOF$_5$: C, 35.83; H, 2.01; N, 6.97. Found: C, 35.10; H, 2.52; N, 7.21.

Preparation 1

5-Trifluoromethyl-4-methyl-3-aminoisoxazole

A 8% solution of sodium bicarbonate (288 ml, 0.27 mole, 1.5 eq.) was added to 96% hydroxylamine hydrochloride (19.54 g, 0.27 mole, 1.5 eq.) dissolved in water (180 ml), with stirring at below 10° C. to form free hydroxylamine and then crude 2-(trifluoroaceto)propionitrile (27.72 g, 0.18 mole) obtained from Example 3(a) was added to this mixture (pH of the reaction mixture became 6.2). After heating under reflux for 8 hours, 36% hydrochloric acid (15.3 ml, 0.178 mole, 1.0 eq.) was added and the mixture was heated under reflux to react for an additional hour (to cyclize the oxime compound). After completion of the reaction, a 48% solution of sodium hydroxide were added dropwise to adjust pH 10 or higher, while cold and the mixture was extracted with methylene chloride. After the extract was dried with anhydrous sodium sulfate, methylene chloride was evaporated and the resulting residue was purified by column chromatography on silica gel (Lobar column) to give 9.49 g (31.7%) of the title compound as colorless crystals, m.p. 34.5°–36.0° C., b.p. 65°–70° C./0.78 mmHg. Anal. Calcd. for C$_5$H$_5$N$_2$OF$_3$: C, 36.15; H, 3.04; N, 16.87. Found: C, 36.20; H, 3.10; N, 16.84.

The structure of this product was also comfirmed by IR, NMR and UV.

3-Trifluoromethyl-4-methyl-5-aminoisoxazole was also obtained. Yield: 0.79 g (2.6%), b.p. 85°–87° C./12 mmHg.

Preparation 2

5-Trifluoromethyl-3-aminoisoxazole

In water (15 ml) was dissolved 96% hydroxylamine hydrochloride (1.63 g, 0.0225 mole, 1.5 eq.). A 8% solution of sodium bicarbonate (24 ml, 0.0225 mole, 1.5 eq.) was added to the solution with stirring at below 10° C. to form free hydroxylamine. Crude trifluoroacetoacetonitrile (2.16 g, 0.015 mole) was then added to this mixture and the mixture was heated under reflux for 2.5 hours. After the addition of 36% hydrochloric acid (5.7 ml), the mixture was heated under reflux to react for additional one hour. After completion of the reaction, a 48% solution of sodium hydroxide was added dropwise to adjust to pH 10 or higher while cold and the mixture was extracted with methylene chloride. After the extract was dried with anhydrous sodium sulfate, methylene chloride was evaporated and the resulting residue was purified by column chromatography on silica gel (Lobar column) to give the mixture (0.60 g, 26.0%) of the title compound and 3-trifluoromethyl-5-aminoisoxazole (the ratio of both by NMR measurement was 4.4:95.6).

Preparation 3

5-Pentafluoroethyl-3-aminoisoxazole

The title compound was obtained according to the same procedure as described in Preparation 1 except that crude pentafluoropropionylacetonitrile (2.20 g, 0.010 mole) and water (10 ml) were used. Yield: 0.0104 g (0.5%). 3-Pentafluoroethyl-5-aminoisoxazole was also obtained. Yield: 0.025 g (1.2%).

Preparation 4

5-Pentafluoroethyl-4-methyl-3-aminoisoxazole

The title compound was obtained as colorless crystals according to the same procedure as described in Preparation 1 except that 2-(pentafluoropropionyl)propionitrile (25.11 g, 0.12 mole), water (120 ml) and 36% hydrochloric acid (10.2 ml) were used. Yield: 9.04 g (34.9%), m.p. 32°–34° C., b.p. 86°–87° C./2.7 mmHg.

Anal. Calcd. for C$_6$H$_5$N$_2$OF$_5$: C, 33.34; H, 2.34; N, 12.96. Found: C, 33.09; H, 2.54; N, 13.06.

3-Pentafluoroethyl-4-methyl-5-aminoisoxazole was also obtained. Yield: 0.96 g (3.7%).

Preparation 5

5-Trifluoromethyl-3-aminoisoxazole

Dry methanol (220 ml) and 96% hydroxylamine hydrochloride (11.52 g, 0.159 mole) were added to trifluoroacetoacetonitrile (16.78 g, 0.122 mole) and the mixture was heated under reflux with stirring for 68 hours. Methanol was then evaporated under reduced pressure and, after addition of water (240 ml), a 48% solution of sodium hydroxide was added to the resulting residue to adjust to pH 11 or higher. The solution was extracted with methylene chloride and, after drying the extract with anhydrous sodium sulfate, the solvent was evaporated under reduced pressure to give the title compound (10.30 g, 55.2%) as little colored crystals, m.p. 57°–58° C., b.p. 66°–67° C./0.8 mmHg.

Preparation 6

3-Pentafluoroethyl-5-aminoisoxazole

The title compound was obtained as colorless plates according to the same procedure as described in Preparation 5 except pentafluoropropionylacetonitrile (2.85 g, 0.015 mole) was used. Yield: 2.31 g (76.2%), m.p. 86°–87° C., b.p. 89°–90° C./3 mmHg.

Preparation 7

3(5)-Trifluoromethyl-5-(3)-aminopyrazole

Benzene (75 ml), acetic acid (6.31 g, 0.105 mole) and 90% hydrazine hydrate (5.44 g, 0.0975 mole) were added to crude trifluoroacetoacetonitrile (9.95 g, 0.075 mole) and the mixture was heated under reflux for 3 hours. After completion of the reaction, water (25 ml) was added and then a 48% solution of sodium hydroxide was added to adjust the pH of the reaction mixture to pH 9–10. The layers were separated and the aqueous layer was extracted with methylene chloride. The organic phase was combined with the benzene layer to evaporate the solvent under the atmospheric pressure. The resulting residue was purified by column chromatography on silica gel to give 3.33 g (29.4%) of the title compound as crystals, b.p. 96.0°–98.5° C./0.13 mmHg, m.p. 94.0°–95.0° C.

What is claimed is:

1. A process for producing a

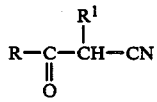

which comprises reacting a compound of the formula:

with a compound of the formula:

in the presence of lithium diisopropylamide or n-butyllithium and a solvent at a temperature and time sufficient to produce said $\beta$-ketonitrile, said reaction being a condensation reaction, and where R is a perfluorinated alkyl having 1 to 3 carbon atoms and $R^1$ is hydrogen or alkyl having 1 to 5 carbon atoms and $R^3$ is an alkyl group.

2. A process according to claim 1 wherein the solvent is selected from the group consisting of tetrahydrofuran and diethyl ether.

3. A process according to claim 1 in which the process is carried out at a temperature of $-78°$ to $0°$ C.

4. A process according to claim 2 in which the solvent is tetrahydrofuran.

* * * * *